United States Patent [19]

Ferrini et al.

[11] Patent Number: 4,804,661
[45] Date of Patent: Feb. 14, 1989

[54] DISUBSTITUTED PIPERAZINES

[75] Inventors: Pier G. Ferrini, Binningen; Andreas v. Sprecher, Oberwil, both of Switzerland

[73] Assignee: Ciba-Geigy Corporation, Ardsley, N.Y.

[21] Appl. No.: 59,898

[22] Filed: Jun. 9, 1987

[30] Foreign Application Priority Data

Jun. 16, 1986 [CH] Switzerland .......................... 2420/86

[51] Int. Cl.$^4$ .................. A61K 31/495; C07D 295/10
[52] U.S. Cl. ...................................... 514/255; 544/391; 544/403
[58] Field of Search ......................... 544/391; 514/255

[56] References Cited

U.S. PATENT DOCUMENTS

| | | | |
|---|---|---|---|
| 3,000,892 | 9/1961 | Janssen | 260/268 |
| 3,625,965 | 12/1971 | Irikura et al. | 544/391 |
| 3,917,617 | 11/1975 | Razdan et al. | 260/293.77 |
| 3,926,961 | 12/1975 | Ferrini et al. | 260/239.7 |
| 4,492,698 | 1/1985 | Björk et al. | 544/391 |

FOREIGN PATENT DOCUMENTS

| | | |
|---|---|---|
| 98713 | 1/1984 | European Pat. Off. |
| 171636 | 2/1986 | European Pat. Off. |
| 1292932 | 4/1962 | France ........................ 544/391 |
| 50-151885 | 12/1975 | Japan ........................... 544/391 |
| 874096 | 8/1961 | United Kingdom ........... 544/391 |

OTHER PUBLICATIONS

Chem. Abstr. 57:12488i.
Chem. Abstr. 57:15126 (1962).
Chem. Abstr. 58:3444e.
Chem. Abstr. 58:4583f.
Chem. Abstr. 58:10211g.
Chem. Abstr. 62:4039f (1965).
Chem. Abstr. 68:87274t (1968).
Chem. Abstr. 68:114642v (1968).
Chem. Abstr. 71:59406f (1969).
Chem. Abstr. 75:76845y (1971).
Chem. Abstr. 78:147915w (1973).
Chem. Abstr. 87:33511s (1977).
Chem. Abstr. 93:8212m (1980).
Chem. Abstr. 93:46713h (1980).
Chem. Abstr. 97:6257p (1982).
Chem. Abstr. 97:72108s (1982) p. 607.
Chem. Abstr. 100:91371u (1984).
Chem. Abstr. 100:209870m (1984).
Chem. Abstr. 82:140186h (1975).
Chem. Abstr. 82:140189m (1975).
Chem. Abstr. 85:94405r (1976).
Chem. Abstr. 88:89712w (1978).
Chem. Abstr. 90:103673j (1979).
Chem. Abstr. 93:71808a (1980).
Chem. Abstr. 96:157389p (1982).
Chem. Abstr. 96:162742c (1982).
Chem. Abstr. 99:105277t (1983) p. 590.
Chem. Abstr. 100:22669k (1984).
Chem. Abstr. 100:34564k (1984).
Derwent Abstract 39606k/17 of European 76 996 (4/83).
Derwent Abstract 25174k/11 of East German 157479 (11/82).
Chem. Abstr. 89:36473h (1978).
Chem. Abstr. 83:58749f (1975) p. 4.

*Primary Examiner*—Richard L. Raymond
*Assistant Examiner*—James H. Turnipseed
*Attorney, Agent, or Firm*—Irving M. Fishman; JoAnn Villamizar

[57] ABSTRACT

Piperazines of the formula

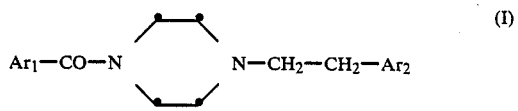

(I)

and their salts, in which each of $Ar_1$ and $Ar_2$, independently of the other, represents phenyl that is unsubstituted or mono- or di-substituted by $C_1$–$C_7$-alkyl, $C_1$–$C_7$-alkoxy, cyano, halogen, trifluoromethyl, amino, $C_1$–$C_7$-alkylamino, di-$C_1$–$C_7$-alkylamino and/or by $C_1$–$C_7$-alkanoylamino, can be used as the active ingredients of medicaments and are manufactured in a manner known per se.

15 Claims, No Drawings

DISUBSTITUTED PIPERAZINES

The invention relates to 1,4-disubstituted piperazines of the formula

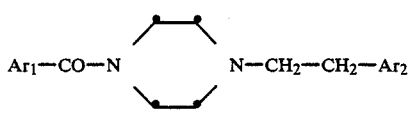

and their salts, in which each of $Ar_1$ and $Ar_2$, independently of the other, represents phenyl that is unsubstituted or mono- or di-substituted by $C_1$–$C_7$-alkyl, $C_1$–$C_7$-alkoxy, cyano, halogen, trifluoromethyl, amino, $C_1$–$C_7$-alkylamino, di-$C_1$–$C_7$-alkylamino and/or by $C_1$–$C_7$-alkanoylamino, to their manufacture and use, to pharmaceutical preparations containing a compound of the formula I or a pharmaceutically acceptable salt thereof, and to their manufacture.

The compounds of the formula I may be in the form of acid addition salts, especially pharmaceutically acceptable acid addition salts. These are formed, for example, with strong inorganic acids, such as mineral acids, for example sulphuric acid, phosphoric acid or hydrohalic acids, with strong organic carboxylic acids, such as $C_1$–$C_4$-alkanecarboxylic acids, for example acetic acid, such as optionally unsaturated dicarboxylic acids, for example oxalic, malonic, maleic or fumaric acid, or such as hydroxycarboxylic acids, for example tartaric acid or citric acid, or with sulphonic acids, such as $C_1$–$C_4$-alkanesulphonic acid or optionally substituted benzenesulphonic acid, for example methane-or p-toluene-sulphonic acid. Corresponding acid addition salts can be formed at one or more basic centres, there being obtained, for example, corresponding mono-or di-piperazinium salts.

Also included are salts that are not suitable for pharmaceutical uses, since these may be used, for example, for the isolation or purification of free compounds according to the invention or their pharmaceutically acceptable salts.

Unless otherwise defined, the general definitions used hereinbefore and hereinafter have especially the following meanings.

$C_1$–$C_7$-alkyl is, for example, methyl, ethyl, propyl, iopropyl, n-butyl, isobutyl, sec.-butyl or tert.-butyl, and also includes corresponding pentyl, hexyl and heptyl radicals. $C_1$–$C_4$-alkyl is preferred.

$C_1$–$C_7$-alkoxy is especially methoxy, ethoxy, propoxy, isopropoxy, butoxy, isobutoxy and sec.- and tert.-butoxy.

Halogen is especially halogen having an atomic number of up to and including 35, such as fluorine, chlorine and bromine, and also iodine.

$C_1$–$C_7$-alkanoyl is especially formyl, acetyl, propionyl, butyryl or pivaloyl. $C_2$–$C_5$-alkanoyl is preferred.

The novel compounds have valuable pharmacological properties. For example, they exhibit, especially, analgesic action, which can be demonstrated, for example, on the basis of the inhibition of the phenyl-p-benzoquinone-induced writhing syndrome in mice in a dose of approximately 0.1 mg/kg p.o. and above.

The analgesic activity is also apparent in the acetic acid writhing test in rats in a dose of approximately 0.1 mg/kg and above, the procedure being analogous to the methodology described in Pain Res. and Therap. Vol. 1, 1976, page 517 (Raven Press N.A.).

Investigations have surprisingly shown that the compounds according to the invention have a novel profile of action. For example, it was found that the compounds of the formula I and their salts do not affect the arachidonic acid cascade and, for example, accordingly cannot be classified as prostaglandin synthetase inhibitors. These compounds also cannot be classified as being of the morphine type.

Accordingly, the compounds of the formula I and their salts can be used, for example, as analgesics for the treatment of pain. The invention also relates to the use of the compounds according to the invention for the manufacture of medicaments, especially analgesics, and for the therapeutic and prophylactic treatment of the human and also the animal body, especially for the treatment of pain. The commercial formulation of the active ingredients can also be included.

The invention relates especially to compounds of the formula I and their salts in which $Ar_2$ represents phenyl that is unsubstituted or mono- or di-substituted by $C_1$–$C_7$-alkyl, $C_1$–$C_7$-alkoxy or by halogen.

The invention relates especially to compounds of the formula I and their salts in which $Ar_1$ represents phenyl that is unsubstituted or mono- or di-substituted by $C_1$–$C_4$-alkyl, $C_1$–$C_4$-alkoxy, halogen, trifluoromethyl, di-$C_1$–$C_4$-alkylamino and/or by $C_1$–$C_5$-alkanoylamino, and $Ar_2$ represents phenyl that is unsubstituted or mo- noor di-substituted by $C_1$–$C_4$-alkoxy or by halogen.

The invention relates especially to compounds of the formula I and their salts in which $Ar_1$ represents phenyl that is monosubstituted by halogen having an atomic number of up to and including 35, such as fluorine or chlorine, especially in the 2- or 4-position, by trifluoromethyl, especially in the 2- or 3-position, by di-$C_1$–$C_4$-alkylamino, such as dimethylamino, especially in the 3-position, or by $C_2$–$C_5$-alkanoylamino, such as acetylamino, especially in the 3-position, or represents phenyl that is disubstituted by $C_1$–$C_4$-alkyl, such as methyl, especially in the 2- and 6-positions, or by $C_1$–$C_4$-alkoxy, such as methoxy, especially in the 3- and 4- or 3- and 5-positions, and $Ar_2$ represents phenyl that is monosubstituted by halogen having an atomic number of up to and including 35, such as fluorine or chlorine, especially in the 4-position.

The invention relates especially to compounds of the formula I and their salts in which $Ar_1$ represents phenyl that is unsubstituted or mono- or di-substituted by $C_1$–$C_4$-alkyl, $C_1$–$C_4$-alkoxy, halogen and/or by trifluoromethyl, and $Ar_2$ represents phenyl that is monosubstituted by halogen.

The invention relates especially to compounds of the formula I and their salts in which $Ar_1$ represents phenyl that is unsubstituted or mono- or di-substituted by $C_1$–$C_4$-alkyl, $C_1$–$C_4$-alkoxy, halogen and/or by trifluoromethyl, and $Ar_2$ represents phenyl that is monosubstituted by $C_1$–$C_4$-alkoxy.

The invention relates more especially to compounds of the formula I and their salts in which $Ar_1$ represents 3,5-di-$C_1$–$C_4$-alkoxyphenyl, especially 3,5-dimethoxyphenyl, and $Ar_2$ represents 4-halophenyl, especially 4-chlorophenyl.

The invention relates more especiallyto compounds of the formula I and their salts in which $Ar_1$ represents 2- or 4-fluorophenyl, 2- or 4-chlorophenyl, 2- or 3-trifluoromethylphenyl, 3- or 4-dimethylaminophenyl, 3- or 4-acetylaminophenyl, 3,4- or3,5-dimethoxyphenyl or 2,6-dimethylphenyl, and $Ar_2$ represents 4-fluoro- or 4-chloro-phenyl.

The invention relates more especially to compounds of the formula I and their salts in which $Ar_1$ represents 2- or 4-fluorophenyl, 3-trifluoromethylphenyl, 4-chlorophenyl, 3- or 4-dimethylaminophenyl or 3- or 4-acetylaminophenyl, and $Ar_2$ represents 4-fluoro- or 4-chloro-phenyl.

The invention relates more especially to compounds of the formula I and their salts in which $Ar_1$ represents phenyl that is monosubstituted by methyl, methoxy, fluorine, chlorine or by trifluoromethyl or that is disubstituted by methoxy, and $Ar_2$ represents phenyl that is monosubstituted by fluorine or chlorine.

The invention relates more especially to compounds of the formula I and their salts in which $Ar_1$ represents phenyl that is monosubstituted by methyl or fluorine, and $Ar_2$ represents phenyl that is monosubstituted by fluorine or chlorine, especially 4-fluoro- or 4-chloro-phenyl.

The invention relates more especially to compounds of the formula I and their salts in which $Ar_1$ represents 2- or 4-fluorophenyl, 2-methylphenyl or 3,5-dimethoxyphenyl, and $Ar_2$ represents 4-fluoro- or 4-chloro-phenyl.

The invention relates especially to the novel compounds mentioned in the Examples and to processes for their manufacture.

The invention relates also to processes for the manufacture of the compounds according to the invention. The manufacture of compounds of the formula I and their salts is effected in a manner known per se and is characterised, for example, in that (a) a compound of the formula $$Ar_1{-}X_1 \qquad \text{(IIa)},$$

or a salt thereof, in which $X_1$ represents carboxy or reactive functionally modified carboxy, is reacted with a compound of the formula

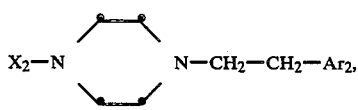

(IIb)

or a salt thereof, in which $X_2$ represents hydrogen or an amino-protecting group, or (b) a compound of the formula

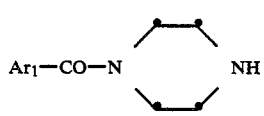

(IIIa)

or a salt thereof is reacted with a compound of the formula $$X_3{-}CH_2{-}CH_2{-}Ar_2 \qquad \text{(IIIb)},$$

or a salt thereof, in which $X_3$ represents hydroxy or reactive esterified hydroxy, or (c) a compound of the formula

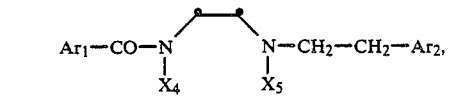

(IV)

or a salt thereof, in which one of the radicals $X_4$ and $X_5$ is hydrogen and the other is a group of the formula $-CH_2-CH_2-X_3$, and $X_3$ represents hydroxy or reactive esterified hydroxy, is condensed intramolecularly, or (d) a compound of the formula

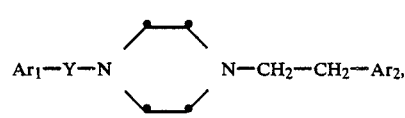

(V)

or a salt thereof, in which Y represents a group that can be oxidised to $-CO-$, is oxidised, or (e) for the manufacture of compounds of the formula I and their salts in which $Ar_1$ represents phenyl that is mono- or di-substituted by $C_1-C_7$-alkoxy, a compound of the formula

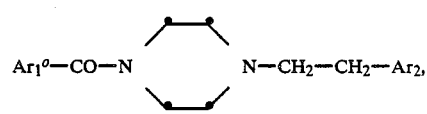

(VI)

or a salt thereof, in which $Ar_1^o$ represents phenyl that is mono- or di-substituted by hydroxy, is alkylated and, if desired, a compound obtained in accordance with the process or by other means is converted into a different compound of the formula I, an isomeric mixture obtained in accordance with the process is separated into its components, a free compound of the formula I obtained in accordance with the process is converted into a salt and/or a salt obtained in accordance with the process is converted into the free compound of the formula I or into a different salt.

The reactions described in the variants hereinbefore and hereinafter are carried out in a manner known per se, for example in the absence, or customarily in the presence, of a suitable solvent or diluent or a mixture thereof, the operation being carried out, as required, while cooling, at room temperature or while heating, for example in a temperature range of approximately from $-78°$ up to the boiling temperature of the reaction medium, preferably from approximately $-10°$ to approximately $150°$ C., and, if necessary, in a closed vessel, under pressure, in an inert gas atmosphere and/or under anhydrous conditions.

The starting materials of the formulae IIa and IIb, IIIa and IIIb, IV, V and VI, which are mentioned hereinbefore and hereinafter and which were developed for the manufacture of the compounds of the formula I and their salts, are in some cases known or they can likewise be manufactured by methods known per se, for example analogously to the process variants described hereinbefore.

In the starting materials, the basic centre can be, for example, in the form of acid addition salts, for example with the acids mentioned above in connection with salts of compounds of the formula I, while starting compounds with acidic groups can form salts with bases.

Suitable salts with bases are, for example, corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-hydroxy-$C_1$–$C_7$-alkylamines, hydroxy-$C_1$–$C_7$-alkyl-$C_1$–$C_7$-alkylamines or polyhydroxy-$C_4$–$C_7$-alkylamines. Cyclic amines are, for example, morpholine, thiomorpholine, piperidine or pyrrolidine. As mono-$C_1$–$C_{C7}$-alkylamines there come into consideration, for example, ethyl- or tert.-butyl-amine, as di-$C_1$–$C_7$-alkylamines there come into consideration, for example, diethyl- or diisopropyl-amine, and as tri-$C_1$–$C_7$-alkylamines there come into consideration, for example, trimethyl- or triethyl-amine. Corresponding hydroxy-$C_1$–$C_7$-alkylamines are, for example, mono-, di- or tri-ethanolamines, and hydroxy-$C_1$–$C_7$-alkyl-$C_1$–$C_7$-alkylamines are, for example, N,N-dimethylamino- or N,N-diethylamino-ethanol, and also glucosamine which is a polyhydroxy-$C_6$-alkylamine.

Reactive functionally modified carboxy $X_1$ is, for example, esterified, especially reactive esterified, carboxy, anhydridised carboxy or amidated carboxy.

Esterified carboxy is, for example, optionally substituted $C_1$–$C_7$-alkoxycarbonyl, such as ethoxycarbonyl, but is preferably reactive esterified carboxy, for example vinyloxycarbonyl that is optionally additionally activated, for example by $C_1$–$C_7$-alkoxy or by optionally substituted carbamoyl, such as 1-$C_1$–$C_7$-alkoxyvinyloxycarbonyl, for example 1-ethoxyvinyloxycarbonyl, or 2-(N-$C_1$–$C_7$-alkylcarbamoyl)-vinyloxycarbonyl, for example 2-(N-ethylcarbamoyl)-vinyloxycarbonyl, and phenoxycarbonyl or thiophenoxycarbonyl each of which is optionally substituted, for example by nitro, halogen, $C_1$–$C_7$-alkanesulphonyl or by phenylazo, such as 4-nitro-, 2,4,5-trichloro-, pentachloro-, 4-methanesulphonyl- or 4-phenylazo-phenoxycarbonyl, thiophenoxycarbonyl or 4-nitrothiophenoxycarbonyl, and also activated methoxycarbonyl, for example methoxycarbonyl substituted by cyano or by optionally esterified carboxy, especially cyanomethoxycarbonyl. Reactive esterified carboxy can also be 1,1- or 1,3-disubstituted 2-isoureidocarbonyl, such as 1,1-di-lower alkyl-, 1,1-diaryl- or 1,1-diaryl-$C_1$–$C_7$-alkyl-2-isoureidocarbonyl, for example 1,1-diethyl-, 1,1-diphenyl- or 1,1-dibenzyl-2-isoureidocarbonyl or 1,3-dicycloalkyl-2-isoureidocarbonyl, for example 1,3-dicyclohexyl-2-isoureidocarbonyl, or N-$C_2$–$C_7$-alkyleneamino-oxycarbonyl, such as N-piperidinyloxycarbonyl, and also N-imido-oxycarbonyl, for example N-succinimido-oxycarbonyl or N-phthalimido-oxycarbonyl.

Anhydridised carboxy is to be understood as being, for example, optionally branched $C_1$–$C_7$-alkoxycarbonyloxycarbonyl, such as ethoxy- or isobutoxycarbonyloxycarbonyl, halocarbonyl, such as chlorocarhalocarbonyl, bonyl, azidocarbonyl, halophosphoryloxycarbonyl, such as dichlorophosphoryloxycarbonyl, or $C_1$–$C_7$-alkanoyloxycarbonyl optionally substituted, for example, by halogen or aryl, such as pivaloyloxycarbonyl, trifluoroacetoxycarbonyl or phenylacetoxycarbonyl. Anhydridised carboxy can also be symmetrically anhydridised carboxy of the formula Ar$_1$—CO—O—CO—.

Reactive amidated carboxy is, for example, 1-imidazolylcarbonyl or 1-pyrazolylcarbonyl each of which is optionally substituted, for example, by $C_1$–$C_7$-alkyl, such as 3,5-dimethylpyrazolylcarbonyl.

An amino-protecting group $X_2$ is, for example, acyl, such as $C_1$–$C_7$-alkanoyl, for example formyl or acetyl, halocarbonyl, such as chlorocarbonyl, and also optionally substituted (hetero)arylsulphonyl, such as 2-pyridyl- or 2-nitrophenyl-sulphonyl.

In the context of the process description hereinbefore and hereinafter, reactive esterified hydroxy, for example $X_3$, unless defined otherwise, is especially hydroxy esterified by a strong inorganic acid or organic sulphonic acid, for example halogen, such as chlorine, bromine or iodine, sulphonyloxy, such as hydroxysulphonyloxy, halosulphonyloxy, for example fluorosulphonyloxy, $C_1$–$C_7$-alkanesulphonyloxy optionally substituted, for example, by halogen, for example methane- or trifluoromethane-sulphonyloxy, $C_3$–$C_7$-cycloalkanesulphonyloxy, for example cyclohexanesulphonyloxy, or benzenesulphonyloxy optionally substituted, for example, by $C_1$–$C_7$-alkyl or halogen, for example p-bromophenyl- or p-toluene-sulphonyloxy.

If, for example, bases are used in the reactions described hereinbefore and hereinafter, there are suitable, for example, unless otherwise stated, alkali metal hydroxides, hydrides, amides, alkoxides, carbonates, triphenylmethylides, di-$C_1$–$C_7$-alkylamides, amino-$C_1$–$C_7$-alkylamides or $C_1$–$C_7$-alkylsilylamides, or naphthaleneamines, $C_1$–$C_7$-alkylamines, basic heterocycles, ammonium hydroxides and also carbocyclic amines. There may be mentioned by way of example: lithium hydroxide, sodium hydroxide, sodium hydride, sodium amide or sodium ethoxide, potassium tert.-butoxide or carbonate, lithium triphenyl methylide or diisopropylamide, potassium 3-(aminopropyl)-amide or bis-(trimethylsilyl)-amide, dimethylaminonaphthalene, di- or triethylamine, pyridine, benzyltrimethylammonium hydroxide, 1,5-diazabicyclo[4.3.0]non-5-ene (DBN) and also 1,8-diazabicyclo[5.4.0]undec-7-ene (DBU).

Variant (a):

The N-acylation in accordance with the process is carried out in a manner known per se, if necessary in the presence of a condensation agent, especially a basic condensation agent. Suitable bases are, for example, representatives of the bases mentioned above. In many cases, the basicity of the compound of the formula IIb is sufficient.

If $X_1$ represents carboxy, there are formed, for example, primarily the corresponding ammonium salts which can be dehydrated by heating or by treatment with suitable dehydrating agents (as condensation agents), such as carbodiimides, for example N,N'-di-lower alkyl- or N,N'-dicycloalkyl-carbodiimide, such as N,N'- diethyl-, N,N'-diisopropyl- or N,N'-dicyclohexylcarbodiimide, advantageously with the addition of N-hydroxysuccinimide or optionally substituted, for example halo-, lower alkoxy- or lower alkylsubstituted, 1-hydroxybenzotriazole or N-hydroxy-5-norbornene-2,3-dicarboxamide, and also N,N-carbonyldiimidazole. Using carbodiimides there may be formed intermediately, for example, also the corresponding 1-isoureidocarbonyl compounds. As water-binding condensation agents there may furthermore be used N-ethoxycarbonyl-2-ethoxy-1,2-dihydroquinoline, phosphoryl cyanamides or phosphoryl azides, such as diehhylphosphoryl cyanamide or diphenylphosphoryl azide, triphenylphosphine disulphide or 1-lower alkyl-2-halopiperidinium halides, such as 1-methyl-2-chloropyridinium iodide.

If the compounds of the formula IIa contain phenyl substituted in position 2 by amino and if $X_1$ represents carboxy, such a compound of the formula IIa may be in the form of a corresponding isatic acid anhydride.

The starting materials used in this process variant are in some cases known or can be manufactured by processes known per se.

For the manufacture of compounds of the formula (IIa) in which $X_1$ represents optionally substituted $C_1$–$C_7$-alkoxycarbonyl, the free acid ($X_1$=carboxy) or an acid anhydride ($X_1$ represents, for example, halocarbonyl) can usually be used as starting material and is reacted, for example, with the corresponding alcohol, which is, if necessary, in reactive form, for example a $C_1$–$C_7$-alkyl halide. The manufacture of compounds of the formula (IIa) in which $X_1$ represents optionally additionally activated vinyloxycarbonyl can be effected, for example, by transesterification of a $C_1$–$C_7$-alkyl ester with vinyl acetate (activated vinyl ester method), by reaction of the free acid of compounds of the formula (IIa) with lower alkoxyacetylene (for example ethoxyacetylene method) or, analogously to the Woodward method, with a 1,2-oxazolium salt. Compounds of the formula (IIa) containing optionally substituted phenoxycarbonyl or thiophenoxycarbonyl can be obtained, for example, starting from the free acid, according to the carbodiimide method, by reaction with the corresponding (thio)phenol. Likewise starting from the free acid of the formula (IIa), it is possible to obtain compounds of the formula (IIa) in which $X_1$ represents activated methoxycarbonyl or 1,1- or 1,3-disubstituted 2-isoureidocarbonyl, for example by reaction with a haloacetonitrile, such as chloroacetonitrile (cyanomethyl ester method) or with a carbodiimide or cyanamide (carbodiimide or cyanamide method), respectively. N-$C_2$–$C_7$-alkyleneamino-oxycarbonyl and N-imido-oxycarbonyl compounds of the formula (IIa) can be manufactured, for example when using the free acid of the formula (IIa), from corresponding N-hydroxy compounds with the aid of carbodiimides according to the activated N-hydroxy esters method. For the manufacture of compounds of the formula (IIa) in which $X_1$ represents optionally branched $C_1$–$C_7$-alkoxycarbonyloxycarbonyl, halophosphoryloxycarbonyl or optionally substituted $C_1$–$C_7$-alkanoyloxycarbonyl, it is possible to use as starting material, for example, the free acid of the formula (IIa) which can be treated, for example, with a corresponding halide, such as an optionally substituted $C_1$–$C_7$-alkylcarbonic acid halide (mixed O-carbonic acid anhydrides method), phosphorus oxyhalide (for example phosphorus oxychloride method) or an optionally substituted $C_1$–$C_7$-alkanoyl halide (mixed carboxylic acid halides method). Azidocarbonyl compounds of the formula (IIa) are obtainable, for example, by treatment of corresponding hydrazides with nitrous acid (azide method). For the manufacture of compounds of the formula (IIa) in which $X_1$ represents optionally substituted 1-imidazolylcarbonyl or 1-pyrazolylcarbonyl, the free acid of the formula (IIa) is reacted, for example, with di-(1-imidazolyl)-carbonyl (imidazolide method) or the relevant hydrazide is reacted, for example, with a corresponding 1,3-di-ketone (pyrazolide method), respectively.

Variant (b):

$X_3$ represents especially reactive esterified hydroxy, preferably halogen, such as chlorine.

The N-alkylation in accordance with the process is carried out in a manner known per se, if necessary in the presence of a base, for example one of the bases mentioned above.

The starting materials used in this process variant are in some cases known or can be manufactured in a manner known per se.

Thus, for example, the starting material of the formula IIIa can be manufactured as follows: a compound of the formula $Ar_1$–$X_1$ (IIa) or a salt thereof in which $X_1$ represents carboxy or reactive functionally modified carboxy is reacted in the manner described in variant a) with a compound of the formula

or a salt thereof, in which $Z_1$ represents hydrogen or an amino-protecting group, such as benzyl, and, if appropriate, the amino-protecting group is removed, for example benzyl is removed by customary hydrogenolysis.

Variant (c):

The intramolecular N-alkylation in accordance with the process is carried out in a manner known per se, if necessary in the presence of a condensation agent, especially a basic condensation agent. As bases there are used, for example, the bases mentioned above.

$X_3$ represents especially reactive esterified hydroxy, preferably halogen, such as chlorine.

The starting material can be manufactured in a manner known per se. For example, a compound of the formula $Ar_1$—$X_1$ (IIa) or a salt thereof in which $X_1$ represents carboxy or reactive functionally modified carboxy is used as starting material and is reacted firstly with a compound of the formula $Ar_2$—$CH_2$—$CH_2$—N-H—$CH_2$—$CH_2$—$NH_2$ (IVa), analogously to variant (a). In the next reaction step, the resulting compound is reacted with a compound of the formula $$X_3\text{—}CH_2\text{—}CH_2\text{—}X_3 \qquad (IVb)$$

under N-alkylating conditions, in accordance with variant (b).

Variant (d):

A group Y that can be oxidised to —CO— is especially —$CH_2$—.

The oxidation of corresponding compounds of the formula V is carried out with the aid of a suitable oxidising agent, there being used preferably tetra-$C_1$–$C_4$-alkylammonium permanganates that are optionally substituted, for example, by a phenyl radical, especially benzyltriethylammonium permanganate.

The starting material of the formula V is manufactured in a manner known per se. For example, a compound of the formula IIb in which $X_2$ represents hydrogen is used as starting material and is reacted, under the N-alkylating conditions described in variant (b), with a compound of the formula $Ar_1$—$CH_2$—$X_6$ (Va), in which $X_6$ represents hydroxy or, especially, reactive esterified hydroxy, especially halogen, such as chlorine or bromine.

Variant (e):

The alkylation can be carried out, for example, with the aid of a corresponding alkylating agent that is known per se. There are suitable as such agents, for example, $C_1$–$C_7$-alkanols and, especially, reactive esterified derivatives thereof. There are preferably used $C_1$–$C_7$-alkyl halides, such as methyl iodide, and also di-$C_1$–$C_7$-alkyl sulphates, such as dimethyl sulphate, diazo-$C_1$-$C_4$-alkanes, such as diazomethane, $C_1$-$C_7$-alkylsulphonates, such as corresponding benzenesulphonates optionally substituted by halogen or $C_1$-$C_7$-alkyl, for example corresponding p-bromophenyl- or p-toluene-sulphonates, tri-$C_1$-$C_7$-alkylsulphonium hydroxides, tri-$C_1$-$C_7$-alkylselenium hydroxides, tri-$C_1$-$C_7$-alkyloxosulphonium hydroxides or tri-$C_1$-$C_7$-alkylanilinium hydroxides, such as trimethylsulphonium, trimethylselenium, trimethyloxosulphonium or trimethylanilinium hydroxide.

When reactive esterified derivatives of $C_1$-$C_7$-alkanols are used, for example a di-$C_1$-$C_7$-alkyl sulphate, the alkylation is carried out especially in the presence of one of the abovementioned bases, preferably in the presence of potassium hydroxide or carbonate, while the reaction with a diazo-$C_1$-$C_4$-alkane is, if necessary, carried out in the presence of a Lewis acid. Lewis acids are, for example, halides of boron, aluminium, tin(II), antimony(III), arsenic(III), silver(I), zinc(II) and iron(III).

The alkylation with a $C_1$-$C_7$-alkanol, such as methanol, is carried out, for example, in the presence of one of the acids mentioned above.

For the manufacture of the starting material of the formula VI, for example a compound of the formula $Ar_1^o$—$X_1$ (VIa) is used and the hydroxy group(s) is/are protected by the introduction of a hydroxy-protecting group, for example by acylation, such as acetylation with acetic anhydride, and the compound so obtained is reacted analogously to variant a) with piperazine that is optionally mono-protected.

A compound according to the invention obtained in accordance with the process or by other means can be converted into a different compound according to the invention in a manner known per se.

In compounds according to the invention in which the radical $Ar_1$ or $Ar_2$ contains a free amino group, that amino group can be mono- or di-substituted in the manner indicated above in variant (a) or (b), that is to say can be N-acylated or N-alkylated, respectively. Likewise, primary or secondary amino groups can be reductively alkylated analogously to the Leuckart-Wallach (or Eschweiler-Clarke) reaction from carbonyl compounds, for example using formic acid as reducing agent.

Compounds of the formula I in which $Ar_1$ and/or $Ar_2$ represent(s) phenyl substituted by amino can be converted in a manner known per se into compounds of the formula I in which $Ar_1$ and/or $Ar_2$ represent(s) phenyl substituted by $C_1$-$C_7$-alkoxy, cyano or by halogen, especially chlorine or fluorine, also bromine or iodine. For that purpose, for example, the amino group is diazotised, for example by treatment with a nitrite, such as an alkali metal nitrite, for example sodium nitrite, or with nitro-lower alkanes in the presence of protonic acids to form the diazonium group —$N_2^\oplus A^\ominus$, in which $\ominus$ represents an anion, such as chloride. The diazonium group can be replaced by cyano in the next reaction step, for example by reaction with cyanides, for example analogously to the Sandmeyer reaction with copper(I) cyanide or alkali metal tetracyanocuprate (I), or, in accordance with the Gattermann reaction, with alkali metal cyanides in the presence of metallic copper. The replacement of the group —$N_2^\oplus A^\ominus$ by halogen can be effected, for example, by treatment with halides, such as copper(I) halides, for example in accordance with the Sandmeyer reaction, or with alkali metal halides in the presence of metallic copper analogously to the Gattermann reaction. Fluorine can also be introduced, for example, by reaction with a tetrafluoroborate in accordance with the Schiemann reaction. If corresponding diazonium compounds are treated with a $C_1$-$C_7$-alkanol, $C_1$-$C_7$-alkoxy can be introduced. In an advantageous modification of these conversion reactions, corresponding diazonium compounds are formed in situ and react further under the particular reaction conditions, without being isolated, to form the corresponding compounds of the formula I.

Salts of the formula (I) can be manufactured in a manner known per se. Thus, for example, acid addition salts of free compounds of the formula (I) are obtained by treatment with an acid or a suitable ion exchange reagent. Salts can be converted in customary manner into the free compounds; acid addition salts can be converted, for example, by treatment with a suitable basic agent.

Depending upon the procedure and reaction conditions, the compounds according to the invention having salt-forming, especially basic, properties may be obtained in free form or in the form of salts.

As a result of the close relationship between the novel compound in free form and in the form of its salts, hereinbefore and hereinafter the free compound or its salts should be understood as meaning also the corresponding salts or the free compound, respectively, where appropriate and expedient.

The novel free compounds, including their salts, can also be obtained in the form of their hydrates or may include other solvents used for crystallisation.

Depending upon the starting materials and procedures chosen, the novel compounds may be in the form of one of the possible isomers or in the form of mixtures thereof, for example, depending upon the number of asymmetric carbon atoms, in the form of pure optical isomers, such as antipodes, or in the form of isomeric mixtures, such as racemates, diastereoisomeric mixtures or mixtures of racemates.

Resulting mixtures of racemates can be separated into the pure isomers or racemates in known manner on the basis of the physico-chemical differences between the constituents, for example by fractional crystallisation.

Resulting racemates can also be separated into the optical antipodes according to known methods, for example by recrystallisation from an optically active solvent, by chromatography over chiral adsorbents, with the aid of suitable microorganisms, by cleaving with specific, immobilised enzymes, by means of the formation of inclusion compounds, for example using chiral crown ethers, in which case only one enantiomer is complexed, or by conversion into diastereoisomeric salts, for example by reaction of a basic end product racemate with an optically active acid, such as a carboxylic acid, for example tartaric or malic acid, or a sulphonic acid, for example camphorsulphonic acid, and separation of the mixture of diastereoisomers obtained in this manner, for example on the basis of their different solubilities, into the diastereoisomers, from which the desired enantiomer can be freed by the action of suitable agents. Advantageously, the more active enantiomer is isolated.

The invention also relates to those forms of the process according to which a compound obtainable as intermediate at any stage of the process is used as starting material and the remaining steps are carried out, or a starting material is used in the form of a derivative or salt, and/or its racemates or antipodes or, especially, is formed under the reaction conditions.

In the process of the present invention it is preferable to use those starting materials which result in the compounds described at the beginning as being especially valuable. The invention relates also to novel starting materials, for example of the formulae IIa, IIb, IIIa, IIIb, IV, V and VI, which were developed specifically for the manufacture of the compounds according to the invention, to their use and to processes for their manufacture, the variables Ar$_1$ and Ar$_2$ having the meanings indicated for the groups of compounds of the formula I that are preferred in each case.

The invention relates also to starting compounds of the formula

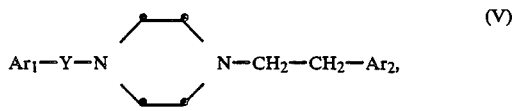

(V)

and their salts, in which Y represents —CH$_2$— and Ar$_1$ and Ar$_2$ have the meanings given for Ar$_1$ and Ar$_2$ in formula I, to their manufacture and use, for example as starting materials for the manufacture of compounds of the formula I, and to pharmaceutical preparations containing such a compound of the formula V or a pharmaceutically acceptable salt thereof. Corresponding compounds of the formula V also have marked analgesic properties. In preferred compounds of the formula V and their salts, the variables Ar$_1$ and Ar$_2$ have the meanings given for the groups of compounds of the formula I that are preferred in each case.

The invention relates also to the use of the compounds of the formula (I) or of pharmaceutically acceptable salts of such compounds having salt-forming properties, especially as pharmacological active ingredients having, especially, analgesic activity. They can be used, preferably in the form of pharmaceutically acceptable preparations, in a method for the prophylactic and/or therapeutic treatment of the animal or human body, especially as analgesics, for example for the treatment of painful conditions, such as migraine.

The invention relates also to pharmaceutical preparations that contain as active ingredients the compounds according to the invention or pharmaceutically acceptable salts thereof, and to processes for their manufacture.

The pharmaceutical preparations according to the invention, which contain the compound according to the invention or pharmaceutically acceptable salts thereof, are for enteral, such as oral and rectal, and parenteral administration, and also for topical administration, to (a) warm-blooded animal(s), the preparations containing the pharmacological active ingredient alone or together with a pharmaceutically acceptable carrier. The daily dose of the active ingredient depends upon age and individual condition and upon the method of administration.

The novel pharmaceutical preparations contain, for example, from approximately 10% to approximately 80%, preferably from approximately 20% to approximately 60%, of active ingredient. Pharmaceutical preparations accoding to the invention for enteral and parenteral administration are, for example, those in dosage unit forms, such as dragées, tablets, capsules or suppositories, and also ampoules. They are manufactured in a manner known per se, for example by means of conventional mixing, granulating, confectioning, dissolving or lyophilising processes. Thus, pharmaceutical preparations for oral use can be obtained by combining the active ingredient with solid carriers, optionally granulating a resulting mixture, and processing the mixture or granulate, if desired or necessary after the addition of suitable adjuncts, to form tablets or dragée cores.

Suitable carriers are, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes using corn, wheat, rice or potato starch, gelatine, tragacanth, methylcellulose and/or polyvinylpyrrolidone, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable coatings that may be resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents or solvent mixtures, or, for the manufacture of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatine, and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

There come into consideration as rectally administrable pharmaceutical preparations, for example, suppositories that consist of a combination of the active ingredient and a suppository base. Suitable as suppository bases are, for example, natural or synthetic triglycerides, paraffin hydrocarbons, polyethylene glycols or higher alkanols. It is also possible to use gelatine rectal capsules that contain a combination of the active ingredient and a base material. Suitable base materials are, for example, liquid triglycerides, polyethylene glycols or paraffin hydrocarbons.

Suitable for parenteral administration are especaally aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran and, optionally, also stabilisers.

The dosage of the active ingredient depends upon the species of warm-blooded animal, age and individual condition, and on the method of administration. In normal cases, the estimated approximate daily dose for a warm-blooded animal weighing approximately 75 kg is, in the case of oral administration, from approximately 100 mg to approximately 1000 mg, advantageously in several equal partial doses.

The following Examples illustrate the invention described above but are not intended to limit the scope thereof in any way. Temperatures are given in degrees Celsius and pressure in Pa.

EXAMPLE 1

A solution of 4.65 g of 4-chlorobenzoyl chloride in 50 ml of methylene chloride is added dropwise, over a period of 10 minutes, to a solution, stirred at room temperature, of 5 g of 1-[2-(4-chlorophenyl)-ethyl]-piperazine in 75 ml of methylene chloride. The reaction mixture is heated under reflux for 5 minutes, allowed to stand at room temperature for 1 hour and then concentrated by evaporation. The residue is made into a slurry with hot acetone and, after the addition of hexane, the whole is filtered. 1-[2-(4-chlorophenyl)-ethyl]-4-(4-chlorobenzoyl)-piperazine is obtained and can be purified and characterised via the hydrochloride which has a melting point of 254°–254.5° (decomposition).

EXAMPLE 2

The following are obtained in a manner analogous to that described in Example 1: from 3-chlorobenzoyl chloride: 1-[2-(4-chlorophenyl)ethyl]-4-(3-chlorobenzoyl)-piperazine hydrochloride having a melting point of 221°–223° (decomposition), from 2-chlorobenzoyl chloride: 1-[2-(4-chlorophenyl)ethyl]-4-(2-chlorobenzoyl)-piperazine hydrochloride having a melting point of 230°–233° (decomposition), from 2,6-dichlorobenzoyl chloride: 1-[2-(4-chlorophenyl)-ethyl]-4-(2,6-dichlorobenzoyl)-piperazine hydrochloride having a melting point of from 250° (decomposition), from 2-fluorobenzoyl chloride: 1-[2-(4-chlorophenyl)-ethyl]-4-(2-fluorobenzoyl)-piperazine hydrochloride having a melting point of 215°–218°, from 2,4-dichlorobenzoyl chloride: 1-[2-(4-chlorophenyl)-ethyl]-4-(2,4-dichlorobenzoyl)-piperazine hydrochloride having a melting point of from 240° (decomposition), from 4-fluorobenzoyl chloride: 1-[2-(4-chlorophenyl)-ethyl]-4-(4-fluorobenzoyl)-piperazine hydrochloride having a melting point of from 222° (decomposition), from 3,4-dichlorobenzoyl chloride: 1-[2-(4-chlorophenyl)-ethyl]-4-(3,4-dichlorobenzoyl)piperazine hydrochloride having a melting point of from 240° (decomposition), and from 3-fluorobenzoyl chloride: 1-[2-(4-chlorophenyl)-ethyl]-4-(3-fluorobenzoyl)-piperazine hydrochloride having a melting point of 195°–198° (decomposition).

EXAMPLE 3

4.7 g of isatic acid anhydride are heated to 80°–90° in 60 ml of absolute dioxan. A solution of 6.3 g of 1-[2-(4-chlorophenyl)-ethyl]-piperazine in 70 ml of absolute dioxan is added thereto. The whole is boiled under reflux for 1 hour and concentrated to dryness by evaporation in vacuo, and then the viscous oil is chromatographed on silica gel. The methylene chloride/acetone (1:1) eluate is concentrated by evaporation and dissolved in methanol, and the resulting 1-[2-(4-chlorophenyl)-ethyl]-4-(2-aminobenzoyl)-piperazine is converted into the hydrochloride using methanolic hydrochloric acid. 1-[2-(4-chlorophenyl)-ethyl]-4-(2-aminobenzoyl)-piperazine hydrochloride having a melting point of 238°–240° is obtained.

EXAMPLE 4

In a manner analogous to that described in Example 3, 1-(2-phenylethyl)-4-(2-aminobenzoyl)piperazine having a melting point of 124°–126° is obtained directly, without chromatography, from 8.7 g of isatic acid anhydride and 10.1 g of 1-(2-phenylethyl)-piperazine.

EXAMPLE 5

11.23 g of 1-[2-(4-chlorophenyl)-ethyl]piperazine are dissolved in 100 ml of methylene chloride and there are added thereto 9 ml of triethylamine and then, dropwise and with external cooling, 11.08 g of 3-methoxybenzoyl chloride in 100 ml of methylene chloride. The reaction mixture is stirred overnight at room temperature and is then extracted by shaking once with 50 ml of 2N sodium hydroxide solution and twice with 100 ml of water each time. After being dried over sodium sulphate, the mixture is concentrated to dryness by evaporation in vacuo. The oily 1-[2-(4-chlorophenyl)-ethyl]-4-(3-methoxybenzoyl)piperazine is dissolved in isopropanol, and alcoholic hydrochloric acid is added thereto. After the addition of ether, the crystals are filtered. 1-[2-(4-chlorophenyl)-ethyl]-4-(3-methoxybenzoyl)-piperazine hydrochloride having a melting point of 230°–232° is obtained.

EXAMPLE 6

In a manner analogous to that described in Example 5, 1-[2-(4-chlorophenyl)-ethyl]-4-(3,4-dimethoxybenzoyl)-piperazine having a melting point of 123°–125° is obtained from 11.23 g of 1-[2-(4-chlorophenyl)-ethyl]-piperazine and 13 g of 3,4-dimethoxybenzoyl chloride.

EXAMPLE 7

22.4 g of 1-[2-(4-chlorophenyl)-ethyl]piperazine and 12.1 g of triethylamine are dissolved in 200 ml of dichloromethane, and a solution of 20.4 g of 4-methoxybenzoyl chloride in 30 ml of dichloromethane is added dropwise, while stirring, at 25°–30°. Stirring is continued overnight at room temperature and then the whole is washed in succession with 150 ml of 2N sodium hydroxide solution and with water, dried over sodium sulphate and concentrated to dryness by evaporation. The residue is crystallised from ethanol. 1-[2-(4-chlorophenyl)-ethyl]-4-(4-methoxybenzoyl)piperazine having a melting point of 105°–106° is obtained.

EXAMPLE 8

In a manner analogous to that described in Example 7 it is possible to manufacture 1-[2-(4-chlorophenyl)-ethyl]-4-(4-methylbenzoyl)-piperazine having a melting point of 105°–106°, starting from 22.4 g of 1-[2-(4-chlorophenyl)-ethyl]-piperazine and 18.6 g of 4-methylbenzoyl chloride.

EXAMPLE 9

In a manner analogous to that described in Example 7 it is possible to manufacture 1-[2-(4-chlorophenyl)-ethyl]-4-(2-methoxybenzoyl)-piperazine having a melting point of 114°–115°, starting from 22.4 g of 1-[2-(4-chlorophenyl)-ethyl]-piperazine and 12.7 g of 2-methoxybenzoyl chloride.

EXAMPLE 10

In a manner analogous to that described Example 7 it is possible to manufacture 1-[2-(4-chlorophenyl)-ethyl]-4-(5-cyano-2-methoxybenzoyl)-piperazine having a melting point of 164°–165°, starting from 18.2 g of 1-[2-(4-chlorophenyl)-ethyl]piperazine and 17.5 g of 2-methoxy-5-cyanobenzoyl chloride.

EXAMPLE 11

In a manner analogous to that described in Example 7 it is possible to manufacture 1-[2-(4-methoxyphenyl)-ethyl]-4-(3,4-dimethoxybenzoyl)piperazine having a melting point of 120°–120.5°, starting from 22 g of 1-[2-(4-methoxyphenyl)-ethyl]piperazine and 24 g of 3,4-dimethoxybenzoyl chloride.

EXAMPLE 12

In a manner analogous to that described in Example 7, 1-[2-(4-methoxyphenyl)-ethyl]-4-(3-methoxybenzoyl)-piperazine is obtained starting from 26.9 g of 1-[2-(4-methoxyphenyl)-ethyl]-piperazine and 25 g of 3-methoxybenzoyl chloride. The hydrochloride melts at 188.5°–191°.

EXAMPLE 13

In a manner analogous to that described in Example 7 it is possible to manufacture 1-[2-(3-chlorophenyl)-ethyl]-4-(3,4-dimethoxybenzoyl)piperazine having a melting point of 116°–117°, starting from 8.5 g of 1-[2-(3-chlorophenyl)-ethyl]piperazine and 9.1 g of 3,4-dimethoxybenzoyl chloride.

The starting material can be manufactured, for example, as follows:

50 ml of ethanol, 50 g of potassium hydroxide and 8.8 ml of water are added to 39.8 g of 1-ethoxycarbonyl-4-[2-(3-chlorophenyl)-ethyl]-piperazine, obtainable by reacting 17.7 g of 1-ethoxycarbonylpiperazine and 24.6 g of 2-(3-chlorophenyl)-ethyl bromide while heating at 120°–125° under nitrogen, and the whole is heated under reflux for 3 hours. The whole is then allowed to cool, is diluted with 300 ml of water and 300 ml of toluene and shaken thoroughly, and then the organic phase is separated off, washed with saturated sodium chloride solution, dried over sodium sulphate and concentrated to dryness by evaporation under reduced pressure. 1-[2-(3-chlorophenyl)-ethyl]piperazine is obtained and can be purified via the hydrochloride (m.p. 260°) from which it can then be freed again by treatment with sodium hydroxide solution, separation with diethyl ether and evaporation of the latter.

EXAMPLE 14

In a manner analogous to that described in Example 7 it is possible to manufacture 1-[2-(3-chlorophenyl)-ethyl]-4-(3-methoxybenzoyl)-piperazine starting from 7.2 g of 1-[2-(3-chlorophenyl)-ethyl]piperazine and 6.54 g of 3-methoxybenzoyl chloride. The hydrochloride melts at 197°–198°.

EXAMPLE 15

In a manner analogous to that described in Example 7 it is possible to manufacture 1-(2-phenylethyl)-4-(3,4-dimethoxybenzoyl)-piperazine having a melting point of 107.5°–108.5°, starting from 23.0 g of 1-(2-phenylethyl)-piperazine and 29.1 g of 3,4-dimethoxybenzoyl chloride.

EXAMPLE 16

In a manner analogous to that described in Example 7 it is possible to manufacture 1-(2-phenylethyl)-4-(3-methoxybenzoyl)-piperazine, starting from 25 g of 1-(2-phenylethyl)-piperazine and 23.9 g of 3-methoxybenzoyl chloride. The hydrochloride melts at 174°–175°.

EXAMPLE 17

In a manner analogous to that described in Example 7 it is possible to manufacture 1-[2-(4-fluorophenyl)-ethyl]-4-(3,4-dimethoxybenzoyl)piperazine, starting from 5.3 g of 1-[2-(4-fluorophenyl)-ethyl]-piperazine and 6 g of 3,4-dimethoxybenzoyl chloride. The hydrochloride melts at 121°–123°. It contains 1 mol of ethanol as liquid of crystallisation.

The starting material can be manufactured, for example, as follows:

A solution of 174.14 g of phosphorus tribromide in 80 ml of toluene is added dropwise, while cooling with ice, within a period of 50 minutes, to a solution of 50 g of 2-(4-fluorophenyl)-ethanol in 200 ml of toluene. The whole is stirred for 5 hours at room temperature and poured into 650 ml of ice-water, and then the organic phase is separated off, shaken with 500 ml of toluene, washed with water, dried over sodium sulphate and concentrated to dryness by evaporation under reduced pressure. For the purpose of purification, the crude 2-(4-fluorophenyl)-ethyl bromide is dissolved in chloroform and filtered over 600 g f silica gel.

27.85 g of 2-(4-fluorophenyl)-ethyl bromide are mixed with 21 ml of 1-ethoxycarbonylpiperazine and stirred for 3 hours at 100°. The whole is allowed to cool, is taken up in 400 ml of chloroform and extracted by shaking with 200 ml of 2N sodium hydroxide solution; the organic phase is separated off and dried over sodium sulphate, and the chloroform is evaporated. 1-ethoxycarbonyl-4-[2-(4-fluorophenyl)-ethyl]piperazine remains behind in the form of a light-yellow oil.

37.2 g of 1-ethoxycarbonyl-4-[2-(4-fluorophenyl)ethyl]-piperazine are dissolved in 55 ml of ethanol, and a solution of 47 g of potassium hydroxide in 12.5 ml of water is added dropwise, while stirring. The whole is heated at 115°–120° for 6 hours while stirring, concentrated to dryness by evaporation, taken up in toluene, washed with saturated sodium chloride solution and concentrated to dryness by evaporation under reduced pressure. The 1-[2-(4-fluorophenyl)ethyl]-piperazine which remains behind can be purified via the dihydrochloride which has a melting point of 270°–272°.

EXAMPLE 18

In a manner analogous to that described in Example 7, 1-[2-(4-fluorophenyl)-ethyl]-4-(4-chlorobenzoyl)-piperazine is obtained by reacting 5.7 g of 1-[2-(4-fluorophenyl)-ethyl]-piperazine with 5.7 g of 4-chlorobenzoyl chloride The hydrochloride melts at 239°–241°.

EXAMPLE 19

In a manner analogous to that described in Example 17, 1-[2-(4-fluorophenyl)-ethyl]-4-(4-fluorobenzoyl)-piperazine is obtained by reacting 1-[2-(4-fluorophenyl)-ethyl]-piperazine with 7.2 g of 4-fluorobenzoyl chloride. The hydrochloride melts at 218°–225°.

EXAMPLE 20:

In a manner analogous to that described in Example 17, 1-[2-(4-fluorophenyl)-ethyl]-4-(3-methoxybenzoyl)-piperazine is obtained by reacting 5.3 g of 1-[2-(4-fluorophenyl)-ethyl]-piperazine with 5.1 g of 3-methoxybenzoyl chloride The hydrochloride melts at 206°–208°.

EXAMPLE 21

5 g of 1-[2-(4-chlorophenyl)-ethyl]piperazine are dissolved in 75 ml of dichloromethane, and a solution of 4.65 g of 2-trifluoromethylbenzoyl chloride is added dropwise within a period of 10 minutes. The whole is heated under reflux for 5 minutes, allowed to stand at room temperature for 1 hour, is concentrated to dryness by evaporation, extracted with warm acetone and precipitated with hexane. 1-[2-(4-chlorophenyl)-ethyl]-4-(2-trifluoromethylbenzoyl)-piperazine hydrochloride having a melting point of 212°–214° is obtained.

EXAMPLE 22

In a manner analogous to that described in Example 18, 1-[2-(4-chlorophenyl)-ethyl]-4-(3-trifluoromethylbenzoyl)-piperazine hydrochloride, m.p. 233°–235° (decomposition), or 1-[2-(4-chlorophenyl)-ethyl]-4-(4-trifluoromethylbenzoyl)-piperazine hydrochloride, m.p. 235°–237°, is obtained by reacting 5 g of 1-[2-(4-chlorophenyl)-ethyl]-piperazine with 4.65 g of 3-trifluoromethylbenzoyl chloride or 4.65 g of 4-trifluoromethylbenzoyl chloride, respectively.

EXAMPLE 23

A solution of 18.6 g of p-methylbenzoyl chloride in 30 ml of methylene chloride is added dropwise, over a period of 15 minutes, to a solution, stirred at room temperature, of 22.4 g of 1-[2-(4-chlorophenyl)-ethyl]-piperazine and 12.1 g of triethylamine in 200 ml of methylene chloride. The reaction mixture is stirred overnight at room temperature. The reaction solution is diluted with 100 ml of methylene chloride, washed with 2N NaOH and with water, dried over sodium sulphate and concentrated to dryness by evaporation. The residue is recrystallised twice from alcohol. 1-[2-(4-chlorophenyl)-ethyl]-4-(4-methylbenzoyl)-piperazine having a melting point of 105°–106° is thus obtained.

EXAMPLE 24

A solution of 4.7 g of 2-fluorobenzoyl chloride in 20 ml of methylene chloride is added dropwise, over a period of 10 minutes, to a solution, stirred at room temperature, of 6.6 g of 1-[2-(4-chlorophenyl)-ethyl]-piperazine in 70 ml of methylene chloride. The reaction mixture is stirred overnight at room temperature, diluted with approximately 250 ml of methylene chloride, washed with sodium hydroxide solution and with water, dried over sodium sulphate and concentrated to dryness by evaporation. The residue is purified and characterised via the hydrochloride which has a melting point of 233°–235°. 1-[2-(4-chlorophenyl)-ethyl]-4-(2-fluorobenzoyl)-piperazine hydrochloride is thus obtained.

EXAMPLE 25

A solution of 4.7 g of 2-methylbenzoyl chloride in 50 ml of methylene chloride is added dropwise, over a period of 10 minutes, to a solution, stirred at room temperature, of 13.4 g of 1-[2-(4-chlorophenyl)-ethyl]-piperazine in 100 ml of methylene chloride. The reaction mixture is stirred overnight at room temperature. The suspension is filtered with suction and washed with an ice-cold mixture of methylene chloride and ether, dried and characterised in the form of the hydrochloride which has a melting point of 234-235 5o 1-[2-(4-chlorophenyl)-ethyl]-4-(2-methylbenzoyl)-piperazine hydrochloride is thus obtained.

EXAMPLE 26

A solution of 11.1 g of 2,6-dimethylbenzoyl chloride in 50 ml of methylene chloride is added dropwise, over a period of 10 minutes, to a solution, stirred at room temperature, of 13.5 g of 1-[2-(4-chlorophenyl)-ethyl]-piperazine in 100 ml of methylene chloride. The reaction mixture is stirred overnight at room temperature. The suspension is filtered with suction and washed with ice-cold methylene chloride and finally with ether, dried and characterised in the form of the hydrochloride which has a melting point of 259°–261°. 1-[2-(4-chlorophenyl)-ethyl]-4-(2,6-dimethylbenzoyl)-piperazine hydrochloride is thus obtained.

EXAMPLE 27

A solution of 6.51 g of 3-dimethylaminobenzoyl chloride in 130 ml of methylene chloride is added dropwise, over a period of 10 minutes, to a solution, stirred at room temperature, of 7.97 g of 1-[2-(4-chlorophenyl)-ethyl]-piperazine and 3.6 g of triethylamine in 150 ml of methylene chloride. The reaction mixture is stirred overnight at room temperature, diluted with methylene chloride, rendered alkaline with 2N NaOH and washed with water, dried over sodium sulphate and concentrated to dryness by evaporation. The residue is recrystallised from ethanol. 1-[2-(4-chlorophenyl)-ethyl]-4-(3-dimethylaminobenzoyl)-piperazine having a melting point of 110°–112° is thus obtained.

The 3-dimethylaminobenzoyl chloride is manufactured as follows:

6.66 g of 3-dimethylaminobenzoic acid are dissolved in 20.14 ml of 2N KOH, filtered and concentrated to dryness by evaporation. The crystals so obtained are dried for 6 hours at 90° in a dessicator. 7.85 g of the potassium salt are then suspended in 30 ml of benzene, and 4.9 g of oxalyl chloride in 10 ml of benzene are added dropwise thereto. The whole is stirred for 20 minutes at room temperature and boiled under reflux for 1 hour. The KCl is then filtered off and the benzenic solution is concentrated to dryness by evaporation. A dark red oil is thus obtained, which is immediately reacted further.

EXAMPLE 28

A solution of 5.1 g of 4-dimethylaminobenzoyl chloride in 130 ml of methylene chloride is added dropwise, over a period of 10 minutes, to a solution, stirred at room temperature, of 6.08 g of 1-[2-(4-chlorophenyl)-ethyl]-piperazine and 2.74 g of triethylamine in 150 ml of methylene chloride. The reaction mixture is stirred overnight at room temperature, diluted with methylene chloride, rendered alkaline with 2N NaOH and washed with water, dried over sodium sulphate and concentrated to dryness by evaporation. The residue is recrystallised from ethanol. 1-[2-(4-chlorophenyl)-ethyl]-4-(4-dimethylaminobenzoyl)piperazine having a melting point of 133°–134° is thus obtained.

The 4-dimethylaminobenzoyl chloride is manufactured as follows:

6.66 g of 3-dimethylaminobenzoic acid are dissolved in 20.14 ml of 2N KOH, filtered and concentrated to dryness by evaporation. The crystals so obtained are dried for 6 hours at 90° in a desiccator. 5.5 g of the potassium salt are then suspended in 40 ml of benzene, and 3.4 g of oxalyl chloride in 15 ml of benzene are added dropwise thereto. The whole is stirred for 20 minutes at room temperature and boiled under reflux for 1 hour. The KCl is then filtered off and the benzenic solution is concentrated to dryness by evaporation. Yellow crystals are obtained, which are immediately reacted further.

EXAMPLE 29

A solution of 4-acetaminobenzoic acid anhydride (prepared from 6.97 g of 4-acetaminobenzoic acid in 70 ml of DMF, 3.93 g of triethylamine and 4.22 g of chloroformic acid ethyl ester in 30 ml of chloroform at 0°–5°) is added dropwise, over a period of 10 minutes, to a solution, stirred at room temperature, of 8.73 g of 1-[2-(4-chlorophenyl)-ethyl]piperazine in 50 ml of dimethylformamide and the whole is stirred overnight at room temperature. The reaction solution is concentrated to dryness by evaporation and the residue is dissolved in methylene chloride, rendered alkaline with sodium carbonate solution and washed with water until neutral, dried over sodium sulphate and concentrated by evaporation. The crude product is recrystallised from ethanol and ether. 1-[2-(4-chlorophenyl)-ethyl]-4-(4-acetaminobenzoyl)piperazine having a melting point of 147°–149° is thus obtained.

EXAMPLE 30

71.9 g of 3,5-dimethoxybenzoyl chloride dissolved in 700 ml of $CH_2Cl_2$ are added at room temperature to a solution of 80.5 g of 1-(p-chlorophenethyl)-piperazine in 1200 ml of $CH_2Cl_2$. The rate of addition is so selected that the exothermic reaction remains under control. The whole is then stirred for 15 minutes under reflux and then for a further 1 hour at room temperature. After the addition of 1900 ml of diethyl ether, the whole is stirred for 15 minutes and then the resulting precipitate is filtered off with suction. The precipitate is dissolved in 3.3 litres of boiling ethanol. The colourless precipitate that is obtained after cooling to approximately 20° is filtered off with suction, washed with a little ethanol and dried under a high vacuum for 16 hours at 80°. 1-p-chlorophenethyl-4-(3,5-dimethoxybenzoyl)-piperazine hydrochloride having a melting point of 244°–246° (decomposition) is thus obtained.

The starting material can be manufactured as follows:

72.9 g of 3,5-dimethoxybenzoic acid are suspended in 320 ml of toluene, and 2 drops of dimethylformamide are added thereto. The suspension is heated to 50°. 40 ml of thionyl chloride are added dropwise at that temperature within a period of 10 minutes. The whole is then heated to 90° (vigorous evolution of gas) and stirred for 2 hours. The reaction mixture is cooled and concentrated by evaporation in a rotary evaporator. After the addition of toluene, the whole is again concentrated by evaporation. The oily residue is dried for 15 minutes under a high vacuum. 3,5-dimethoxybenzoyl chloride is thus obtained.

EXAMPLE 31

The following are obtained in a manner analogous to that described in Example 30:

from 3,5-dichlorobenzoyl chloride:

1-(4-chlorophenethyl)-4-(3,5-dichlorobenzoyl)piperazine hydrochloride having a melting point of 239°–241°, from 2,6-dimethoxybenzoyl chloride:

1-(4-chlorophenethyl)-4-(2,6-dimethoxybenzoyl)piperazine hydrochloride having a melting point of 243°–244° (decomposition) (crystallises from methylene chloride/hexane), from 3,5-dimethylbenzoyl chloride:

1-(4-chlorophenethyl)-4-(3,5-dimethylbenzoyl)piperazine hydrochloride having a melting point of 228°–231° (decomposition) (crystallises from ethanol).

EXAMPLE 32

A solution of 4.65 g of 2-trifluoromethylbenzoyl chloride in 50 ml of methylene chloride is added dropwise, over a period of 10 minutes, to a solution, stirred at room temperature, of 5 g of 1-(4-chlorophenethyl)-piperazine in 75 ml of methylene chloride. The reaction mixture is heated under reflux for 5 minutes, allowed to stand at room temperature for 1 hour and then concentrated by evaporation. The residue is made into a slurry with hot acetone and, after the addition of hexane, the whole is filtered. 1-(4-chlorophenethyl)-4-(2-trifluoromethylbenzoyl)piperazine hydrochloride having a melting point of 212°–214° is obtained.

EXAMPLE 33

10 g of 3-acetamidobenzoic acid are dissolved in 100 ml of DMF. At a temperature of from −5° to 0° there are added dropwise, while stirring, firstly 5.65 g of triethylamine and then 6.05 g of chloroformic acid ethyl ester dissolved in 40 ml of $CH_2Cl_2$. The whole is stirred for a further 30 minutes at from 0° to +5° and then, at the same temperature, 12.54 g of 1-(p-chlorophenethyl)-piperazine in 75 ml of DMF are added dropwise. The whole is stirred overnight at room temperature and then concentrated to dryness by evaporation. The residue is taken up in 350 ml of $CH_2Cl_2$ and the whole is washed with 150 ml of 2N NaOH and with 50 ml of $H_2O$ and dried over $Na_2SO_4$. After filtration and concentration by evaporation, a brown oil is obtained, which is caused to crystallise with ether. Recrystallisation is effected from ethanol/ether. 1-[2-(p-chlorophenyl)-ethyl]-4-(3-acetamidobenzoyl)-piperazine having a melting point of 101°–107° is thus obtained.

EXAMPLE 34

3.42 g of benzylpiperazine are dissolved in 35 ml of methylene chloride and there are added thereto 2.1 g of triethylamine and then, dropwise and while cooling with ice, 3.4 g of 3-methoxybenzoyl chloride in 30 ml of methylene chloride. The reaction mixture is stirred overnight at room temperature and then washed with $H_2O$. After being dried over sodium sulphate, the solution is concentrated to dryness by evaporation in vacuo. The oily 1-benzyl-4-(3-methoxybenzoyl)-piperazine is dissolved in 150 ml of fine spirit and debenzylated over 0.5 g of Pd-C. When the hydrogenation is complete, the catalyst is filtered off from the mixture and the filtrate is concentrated to dryness by evaporation in vacuo. The oily N-(3-methoxybenzoyl)-piperazine so obtained is placed in a sulphonating flask with 3.8 g of p-chlorophenethyl bromide and heated to 100°. At 60° a slight exothermic reaction takes place. After 3 hours at 100°, the mixture is cooled and dissolved in 400 ml of methylene chloride, and then 2N NaOH is added thereto; the whole is extracted by shaking and the methylene chloride phase is washed twice with H₂O. The organic phase is dried over Na₂SO₄ and concentrated to dryness by evaporation in vacuo. The oily 1-[2-(4-chlorophenyl)-ethyl]-4-(3-methoxybenzoyl)piperazine is dissolved in isopropanol, and hydrochloric acid is added thereto. After the addition of ether, the hydrochloride, which has a melting point of 230°–232°, crystallises.

EXAMPLE 35

25.2 g of dimethyl sulphate are added carefully to 36.05 g of 1-[2-(4-chlorophenyl)-ethyl]-4-(3,5-dihydroxybenzoyl)-piperazine in 140 ml of 10% potassium hydroxide solution. The reaction mixture is heated at 100° for 30 minutes and extracted with CH₂Cl₂. The combined organic extracts are dried over MgSO₄ and concentrated by evaporation. The oily 1-[2-(4-chlorophenyl)-ethyl]-4-(3,5-dimethoxybenzoyl)piperazine is purified via the hydrochloride which has a melting point of 244°–246° (decomposition).

The starting material can be manufactured, for example, as follows:

50 g of 3,5-dihydroxybenzoic acid are suspended in 132.2 g of acetic anhydride and heated to 50°. After the addition of 15 drops of concentrated H₂SO₄, the resulting solution is stirred for 1 hour at 60°. The reaction mixture is poured onto ice and extracted with CH₂Cl₂. The combined organic phases are washed 3 times with H₂O, dried over Na₂SO₄ and concentrated by evaporation. The residue is crystallised from ether and yields 3,5-diacetoxybenzoic acid having a melting point of 140°–145°.

42 g of 3,5-diacetoxybenzoic acid are heated under reflux for 5 hours with 300 ml of benzene and 26 ml of thionyl chloride. The reaction mixture is concentrated by evaporation and the residue is taken up in benzene and again concentrated by evaporation. 3,5-diacetoxybenzoyl chloride having a melting point of 85°–87° is thus obtained.

In a manner analogous to that described in Example 1, 1-[2-(4-chlorophenyl)-ethyl]-4-(3,5-diacetoxybenzoyl)-piperazine hydrochloride having a melting point of 220° (decomposition) is obtained from 3,5-diacetoxybenzoyl chloride.

A solution of 1-[2-(4-chlorophenyl)-ethyl]-4-(3,5-diacetoxybenzoyl)-piperazine in 500 ml of methanol stirred with 285 ml of 1N NaOH for 16 hours at 20°. The reaction mixture is diluted with H₂O and the pH is adjusted to 6 with acetic acid. The resulting oily precipitate is stirred with CH₂Cl₂ and filtered with suction. Crystallisation from ethanol yields 1-[2-(4-chlorophenyl)-ethyl]-4-(3,5-dihydroxybenzoyl)piperazine having a melting point of 217°–221°.

EXAMPLE 36

A mixture of 5 g of 1-(4-chlorophenethyl)piperazine, 9.25 g of anhydrous potassium carbonate, 4.34 g of 3-trifluoromethylbenzyl chloride and 100 ml of absolute alcohol is heated under reflux for 15 hours while stirring and concentrated by evaporation under reduced pressure. The residue is taken up in water and extracted three times with 70 ml of methylene chloride each time. The combined organic phases are dried over magnesium sulphate and concentrated again to yield a yellow oil which is dissolved in 70 ml of ethyl acetate. The 1-(4-chlorophenethyl)-4-(3-trifluoromethylbenzyl)-piperazine dihydrochloride precipitated by the addition of a solution of hydrogen chloride in ethyl acetate is filtered off with suction and washed with ether. For further purification, the whole is made into a slurry with hot acetone and, after being diluted with hexane, is filtered. M.p. 254°–255° (decomposition).

EXAMPLE 37

The following compounds are manufactured analogously to Example 36:

from 2-fluorobenzyl chloride: 1-(4-chlorophenethyl)-4-(2-fluorobenzyl)-piperazine dihydrochloride having a melting point of 248°–249° (decomposition);

from 4-fluorobenzyl chloride: 1-(4-chlorophenethyl)-4-(4-fluorobenzyl)-piperazine dihydrochloride having a melting point of 265°–268° (decomposition);

from 2-chlorobenzyl chloride: 1-(4-chlorophenethyl)-4-(2-chlorobenzyl)-piperazine dihydrochloride having a melting point of from 240° (decomposition);

from 3-chlorobenzyl chloride: 1-(4-chlorophenethyl)-4-(3-chlorobenzyl)-piperazine dihydrochloride having a melting point of from 260° (decomposition);

from 4-chlorobenzyl chloride: 1-(4-chlorophenethyl)-4-(4-chlorobenzyl)-piperazine dihydrochloride having a melting point of from 250° (slow decomposition);

from 2,4-dichlorobenzyl chloride: 1-(4-chlorophenethyl)-4-(2,4-dichlorobenzyl)-piperazine hydrochloride having a melting point of from 250° (decomposition).

EXAMPLE 38

Tablets containing 25 mg of active ingredient, for example 1-[2-(4-chlorophenyl)-ethyl]-4-(3,5-dimethoxybenzoyl)-piperazine, can be manufactured as follows:

Constituents (for 1000 tablets)

| | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture

All the solid ingredients are firstly forced through a sieve having a mesh width of 0.6 mm and then half the starch is mixed in. The other half of the starch is suspended in 40 ml of water and the resulting suspension is added to a boiling solution of the polyethylene glycol in 100 ml of water and processed with the powder mixture to form a kneadable mass, and the resulting mixture is granulated, if necessary with the addition of water. The granulate is dried overnight at 35°, forced through a sieve having a mesh width of 1.2 mm and compressed to form tablets that are concave on both sides and have a diameter of approximately 6 mm.

EXAMPLE 39

In a manner analogous to that described in Example 38 it is also possible to manufacture tablets that each contain 25 mg of a different compound selected from those mentioned in Examples 1 to 37.

We claim:

1. A piperazine compound of the formula

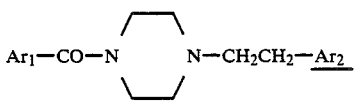 (I)

wherein
Ar₁ is phenyl which is unsubstituted or substituted by one or two substituents selected from $C_{1-4}$ alkoxy, halogen, and trifluoromethyl; and
Ar₂ is phenyl which is monosubstituted by Cl-4 alkoxy or by halogen;
or a pharmaceutically acceptable salt thereof.

2. The compound of claim 1 wherein
Ar₂ is phenyl monosubstituted by halogen;
or a pharmaceutically acceptable salt thereof.

3. The compound of claim 1 wherein
Ar₂ is phenyl monosubstituted by $C_{1-4}$ alkoxy;
or a pharmaceutically acceptable salt thereof.

4. The compound of claim 1 wherein
Ar₁ is 3,5-di-$C_{1-4}$alkoxyphenyl; and
Ar₂ is 4-halophenyl;
or a pharmaceutically acceptable salt thereof.

5. The compound of claim 1 wherein
Ar₁ is 2- or 4-fluorophenyl, 2- or 4-chlorophenyl, 2- or 3-trifluoromethylphenyl, 3,4- or 3,5-dimethoxyphenyl, and
Ar₂ is 4-fluoro or 4-chloro- phenyl;
or a pharmaceutically acceptable salt thereof.

6. The compound of claim 1 wherein
Ar₁ is 2- or 4-fluorophenyl, 3-trifluoromethylphenyl, or 4-chlorophenyl; and
Ar₁ is 4-fluoro- or 4-chloro- phenyl;
or a pharmaceutically acceptable salt thereof.

7. The compound of claim 1 wherein
Ar₁ is phenyl which is (a) monosubstituted by methoxy, fluorine, chlorine, or trifluomethyl or (b) disubstituted by methoxy; and
Ar₂ is phenyl that is monosubstituted by fluorine or chlorine;
or a pharmaceutically acceptable salt thereof.

8. The compound of claim 1 wherein
Ar₁ is phenyl that is monosubstituted by fluorine; and
Ar₂ is phenyl that is monosubstituted by fluorine or chlorine;
or a pharmaceutically acceptable salt thereof.

9. The compound of claim 8 wherein
Ar₂ is 4-fluorphenyl or 4-chlorophenyl;
or a pharmaceutically acceptable salt thereof.

10. The compound of claim 1 wherein
Ar₁ is 2-or 4-fluorophenyl, or 3,5-dimethoxyphenyl; and
Ar₂ is 4-fluorphenyl or 4-chlorophenyl;
or a pharmaceutically acceptable salt thereof.

11. A compound according to claim 1 being
1-2-(4-chlorophenyl)-ethyl-4-(4-chlorobenzoyl)-piperazine,
1-[2-(4-chlorophenyl)-ethyl]-4-(3-chlorobenzoyl)-piperazine,
1-[2-(4-chlorophenyl)-ethyl]-4-(2-chlorobenzoyl)-piperazine,
1-[2-(4-chlorophenyl)-ethyl]-4-(2,6-dichlorobenzoyl)-piperazine,
1-[2-(4-chlorophenyl)-ethyl]-4-(2-fluorobenzoyl)-piperazine,
1-[2-(4-chlorophenyl)-ethyl]-4-(2,4-dichlorobenzoyl)-piperazine,
1-[2-(4-chlorophenyl)-ethyl]-4-(4-fluorobenzoyl)-piperazine,
1-[2-(4-chlorophenyl)-ethyl]-4-(3,4-dichlorobenzoyl)-piperazine,
1-[2-(4-chlorophenyl)-ethyl]-4-(3-fluorobenzoyl)-piperazine,
1-[2-(4-chlorophenyl)-ethyl]-4-(3-methoxybenzoyl)-piperazine,
1-[2-(4-chlorophenyl)-ethyl]-4-(3,4-dimethoxybenzoyl)-piperazine,
1-[2-(4-chlorophenyl)-ethyl]-4-(4-methoxybenzoyl)-piperazine,
1-[2-(4-chlorophenyl)-ethyl]-4-(2-methoxybenzoyl)-piperazine,
1-[2-(4-methoxyphenyl)-ethyl]-4-(3,4-dimethoxybenzoyl)-piperazine,
1-[2-(4-methoxyphenyl)-ethyl]-4-(3-methoxybenzoyl)-piperazine,
1-[2-(3-chlorophenyl)-ethyl]-4-(3,4-dimethoxybenzoyl)-piperazine,
1-[2-(3-chlorophenyl)-ethyl]-4-(3-methoxybenzoyl)-piperazine,
1-[2-(4-fluorophenyl)-ethyl]-4-(3,4-dimethoxybenzoyl)-piperazine,
1-[2-(4-fluorophenyl)-ethyl]-4-(4-chlorobenzoyl)-piperazine,
1-[2-(4-fluorophenyl)-ethyl]-4-(4-fluorobenzoyl)-piperazine,
1-[2-(4-fluorophenyl)-ethyl]-4-(3-methoxybenzoyl)-piperazine,
1-[2-(4-chlorophenyl)-ethyl]-4-(2-trifluoromethylbenzoyl)-piperazine,
1-[2-(4-chlorophenyl)-ethyl]-4-(3-trifluoromethylbenzoyl)-piperazine,
1-[2-(4-chlorophenyl)-ethyl]-4-(4-trifluoromethylbenzoyl)-piperazine,
1-[2-(4-chlorophenyl)-ethyl]-4-(3,5-dichlorobenzoyl)-piperazine,
1-[2-(4-chlorophenyl)-ethyl]-4-(2,6-dimethoxybenzoyl)-piperazine, or a pharmaceutically acceptable salt thereof.

12. A compound according to claim 1 being 1-[2-(4-chlorophenyl)-ethyl]-4-(2-fluorobenzoyl)-piperazine or a pharmaceutically acceptable salt thereof.

13. A compound according to claim 1 being 1-2-(4-chlorophenyl)-ethyl-4-(3,5-dimethoxybenzoyl)-piperazine or pharmaceutically acceptable salt thereof.

14. A analgesic pharmaceutical composition comprising a pharmaceutically effective amount of a compound according to claim 1 or a pharmaceutically acceptable salt thereof in addition to a pharmaceutically acceptable adjunct.

15. A method of treating pain in an animal in need thereof comprising administering to said animal a therapeutically effective amount of a compound of claim 1 or a pharmaceutically acceptable salt thereof.

* * * * *